United States Patent [19]

Harris, Sr. et al.

[11] 4,121,465
[45] Oct. 24, 1978

[54] AUTOMATIC FLUID INJECTOR, AND MAGAZINE THEREFOR

[75] Inventors: Rano J. Harris, Sr.; Rano J. Harris, Jr.; Julius P. Averette, Jr., all of Baton Rouge, La.

[73] Assignee: Precision Sampling Corporation, Baton Rouge, La.

[21] Appl. No.: 817,818

[22] Filed: Jul. 21, 1977

[51] Int. Cl.$^2$ .............................................. G01N 1/14
[52] U.S. Cl. ............................ 73/422 GC; 73/423 A
[58] Field of Search ..................... 73/423 A; 141/130; 23/259; 198/655, 656, 793

[56] References Cited

U.S. PATENT DOCUMENTS

| | | | |
|---|---|---|---|
| 2,698,076 | 12/1954 | Nilsson | 198/656 |
| 3,940,995 | 3/1976 | Harris, Sr. et al. | 73/423 A |
| 4,039,286 | 8/1977 | Keller | 23/259 |

*Primary Examiner*—S. Clement Swisher
*Attorney, Agent, or Firm*—Llewellyn A. Proctor

[57] ABSTRACT

A new and improved magazine for use in automatic fluid injectors, and novel fluid injector for use in accurately measuring and injecting preselected quantitites of fluid specimens, or samples, into various media, e.g., a receptacle or septum inlet of a modern analytical instrument. In its preferred aspects, the invention is comprised of a new and novel magazine-injector combination. The combination is comprised of (a) a fluid injector sub-assembly, inclusive of a barrel on one end of which is mounted a hollow needle providing an opening from the dispensing end of said needle through said needle and barrel, and on the other end valve means for opening the barrel to permit the ingress of fluid specimen into said barrel and needle and for closure of said barrel to interrupt the flow of fluid specimen through said barrel and needle, (b) an injector feed sub-assembly, inclusive of a probe assembly comprising a gas supply conduit with gas inlet and gas outlet means, a fluid specimen supply conduit with fluid specimen inlet means, and outlet means connected to the barrel and operatively associated with the valve means of said fluid injector sub-assembly, and means for puncturing the septum of the fluid specimen containing vial so that the gas supply and fluid specimen supply conduits can enter into and be within the vial, and (c) said magazine.

The magazine is comprised of a closed loop, flexible roller chain upon which fluid vials are carried or transported, in seriatim, past a station for pick-up by the probe assembly of (a) the fluid injector sub-assembly for transfer to the barrel of (b) the injector feed sub-assembly.

7 Claims, 16 Drawing Figures

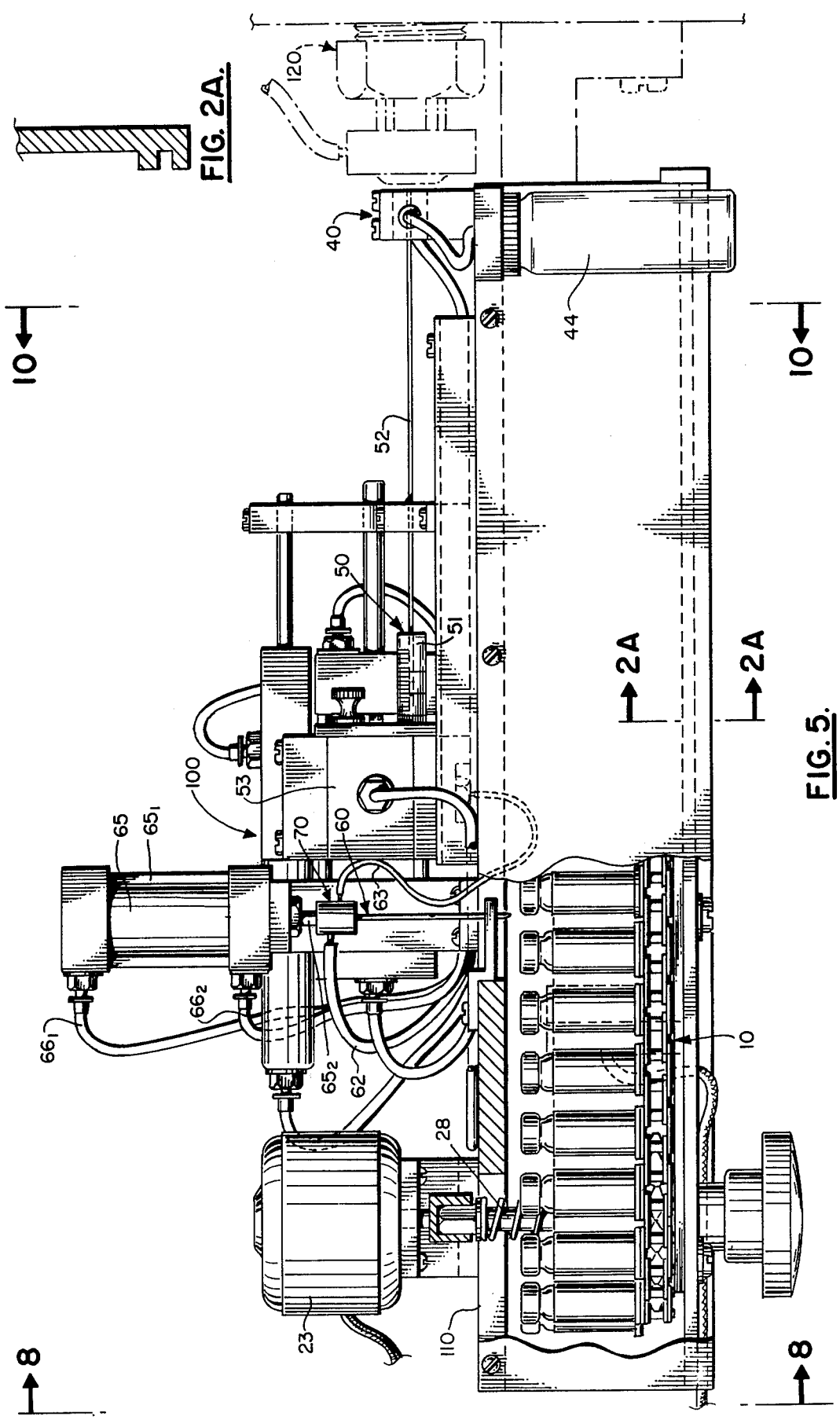

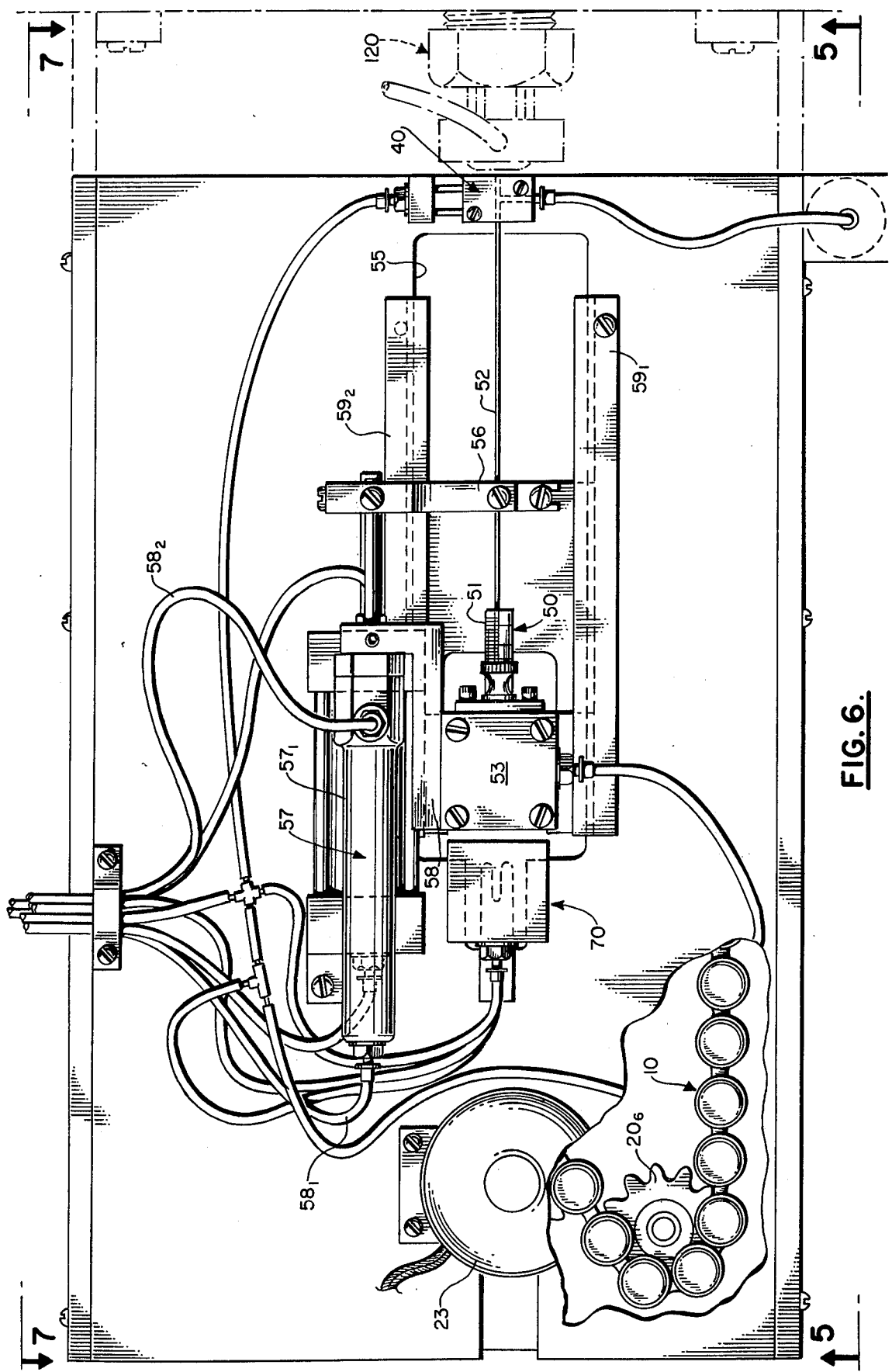

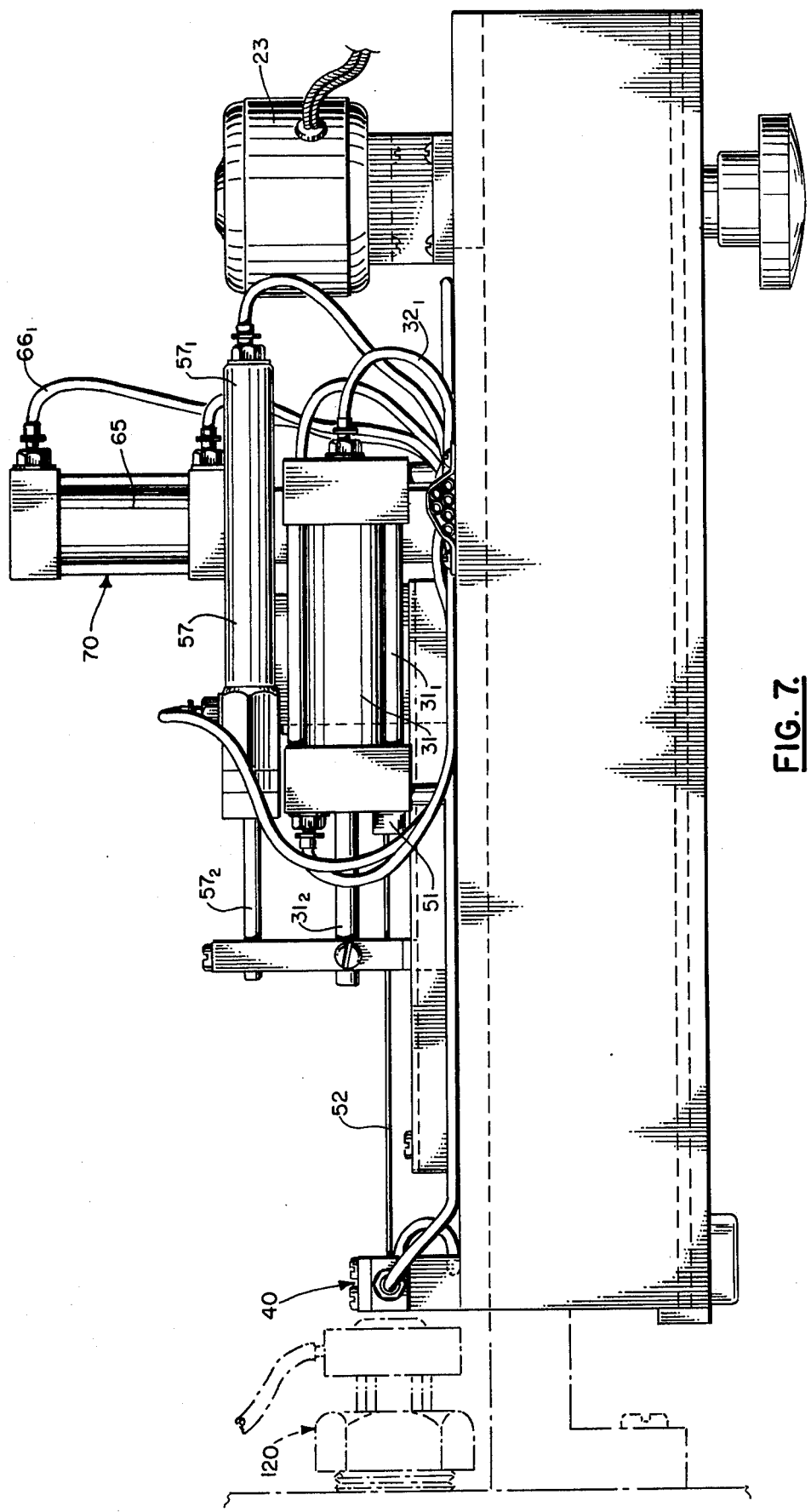

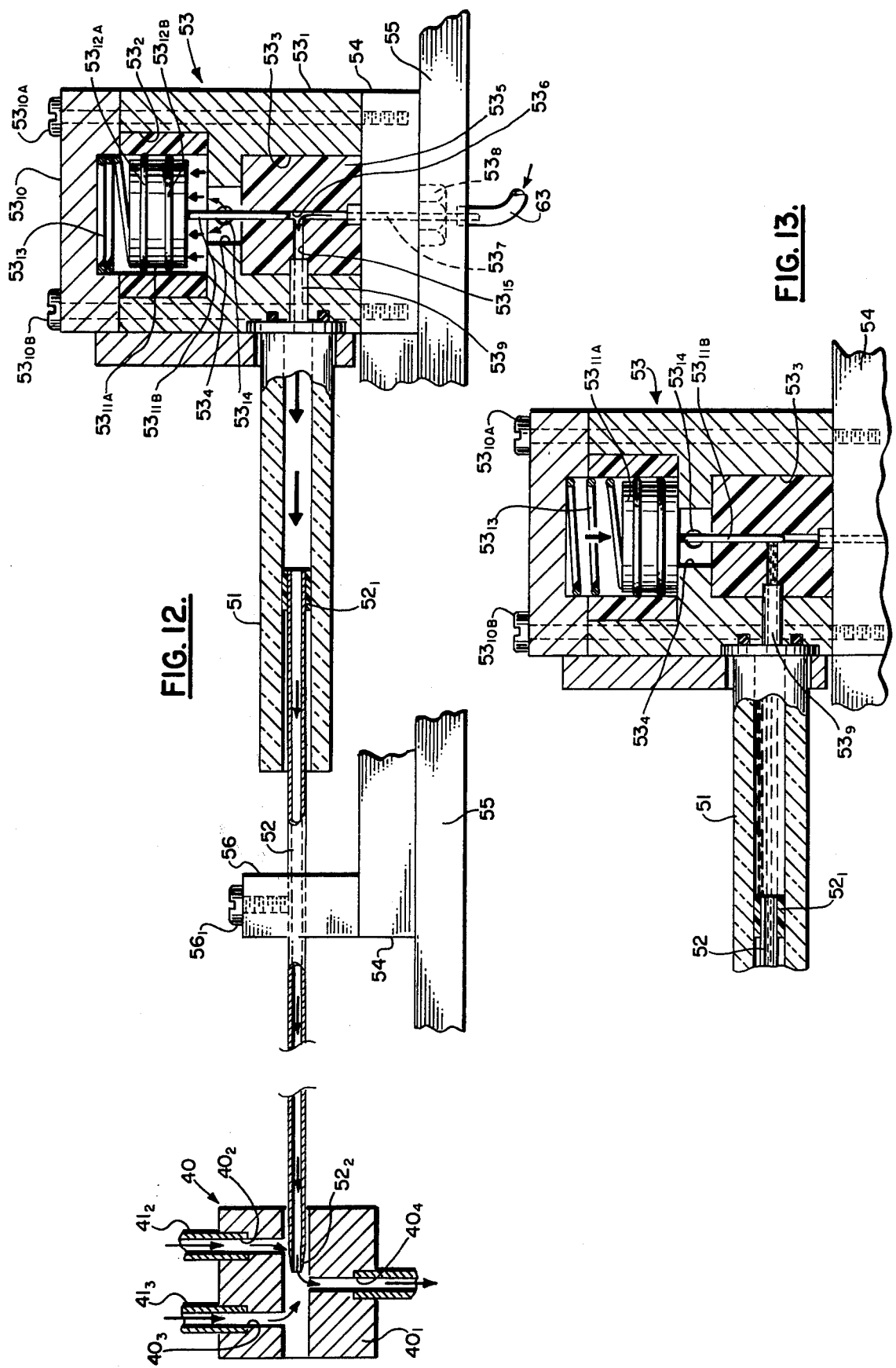

AUTOMATIC FLUID INJECTOR, AND MAGAZINE THEREFOR

The present invention relates generally to automatic fluid injectors, or apparatus, for automatically measuring and injecting accurately measured quantities of fluids. More particularly, it relates to apparatus, especially fluid injection devices, for use in the continuous automatic measurement and injection of very small, accurately measured quantities of gas and liquid specimens into various media, e.g., modern analytical instruments such as mass spectrographs or gas chromatographs.

Fluid injecton devices, particularly needle syringes, have gained wide acceptance by industry, and by the scientific community, generally, for use in dispensing infinitesimally small, accurately measured fluid specimens, e.g., to modern analytical instruments such as mass spectrometers and gas chromatographs. Such syringes embody apparatus comprising a tubular body or barrel, on the forward end of which is fitted a hollow or tubular needle and, usually, at the opposite end a slidable plunger which travels within the bore of the barrel. More recently, devices have been introduced wherein the needle is movable relative to the barrel, and the plunger is replaced by an on-off valve. A fluid specimen is introduced into the barrel and needle by opening the valve, and ejected by closure of the valve with movement of the needle into the rear of the barrel to displace a measured volume of the fluid as claimed in pending Application Ser. No. 749,804 filed Dec. 13, 1976; now U.S. Pat. No. 4,044,616. Fluid injection devices and syringes of such character are capable of dispensing very small fluid specimens, accurately measured, on the order of a few microliters, or very small fractions of a microliter, e.g., from about 0.01 to about 5 microliters, or fractional parts thereof.

In recent years, due to the obvious advantages offered by the combination of automatic fluid injecton instruments, and modern data gathering techniques, which greatly reduce operating manpower without decrease in accuracy, there is considerable demand for improved automated devices of these types.

Accordingly, it is a primary object of the present invention to provide a new and novel magazine for use in fluid injectors, notably fluid injectors readily adaptable to automatically perform the basic cyclic functions of purging and cleaning, filling, and injecting fluid specimens.

A particular object is to provide such apparatus combination capable of continuously cyclically serially withdrawing from said magazine precisely measured, infinitesimally small quantities of gas or liquid specimens from prefilled vials or containers, injecting the specimens in seriatim in reproducible quantities, and cleaning prior to subsequent withdrawal and injection of a subsequent specimen.

Another, and more particular, objective is to provide a magazine of simple and relatively inexpensive construction, particularly one which as a part of an automated fluid injector unit can be readily serviced and operated, and readily adaptable to rapid mass production techniques.

A further object is to provide further improvements over those apparatuses specifically disclosed and claimed in Application Ser. No. 618,374 (U.S. Pat. No. 4,000,654), Ser. No. 749,804 (U.S. Pat. No. 4,044,616), U.S. Pat. Nos. 3,754,443, 3,824,859, 3,885,438, and 3,940,995, supra, each of which is herewith incorporated by reference.

These objects and others are achieved in accordance with the present invention which embodies further improvements in fluid injection devices, notably automated fluid injector systems. A preferred automatic fluid injector is one comprisine (a) a fluid injector sub-assembly, inclusive of barrel and hollow needle slidably mounted therein, and valve for controlling the ingress of fluid specimen into the barrel and needle, (b) an injector feed sub-assembly, or unit, for automatically purging, cleaning and filling the said fluid injector sub-assembly, and, in particular, as a part of the combination, (c) a new and novel magazine for transporting fluid specimen containing vials and positioning same in relation to the injector feed assembly for pick-up of the fluid specimen, and delivery to the barrel and needle portions of the fluid injector sub-assembly. The atomatic fluid injector is provided with automation or control means for repetitively and automatically carrying out the functions of cleaning, purging and filling the barrel and needle of the fluid injector sub-assembly with predetermined quantities of fluid specimens, in timed sequence, and the several sub-assemblies of the automatic fluid injector are generally contained within a housing, or housings. The sub-assemblies constituting (a) the feed injector sub-assembly, (b) the injector feed assembly, and (c) the magazine are preferably contained within a single housing.

In the most preferred apparatus combination (a) the automatic fluid injector is one comprised of a barrel, or hollow tubular member, a hollow needle or cannula slidably mounted within the forward end of said barrel, and an on-off valve located at the rearward end of said barrel for opening and closing the barrel to the flow of a fluid specimen therethrough from a suitable source. In open position, the fluid specimen can be flowed through the valve, barrel and needle to effectively clean these members and, on closure of the valve, a measured amount of the fluid specimen can be trapped inside the barrel and needle for subsequent injection. And then, on thrust of the dispensing end of the needle into a suitable media, e.g., the septum inlet to an analytical instrument, the fluid specimen can be injected by a relative forward movement of the barrel which moves the needle rearwardly into the barrel to displace and cause ejection of the fluid specimen through the dispensing end of the needle and into the inlet of the analytical instrument.

In its preferred aspects the needle, barrel and valve constitute the principal portion of a fluid injector sub-assembly which is mounted upon a movable or slidable plate to which the needle portion thereof is rigidly affixed. Relative motion is provided between the barrel and needle in that the valve and barrel are movable as a unit. In turn, the slide plate is mounted upon a fixed base, or base plate, drive means being provided to move the slide plate with its components, viz. needle, barrel and valve as required for insertion of the dispensing end of the needle into the septum inlet of an analytical instrument. After insertion of the dispensing end of the needle into the septum inlet, ejection of an accurately measured portion of a fluid specimen is provided by drive means which closes the valve, and drive means which effect reciprocation, or movement, of the barrel relative to the needle such that the rearward end of the needle displaces fluid from the barrel to produce ejection thereof.

(b) The injector feed sub-assembly is comprised of a hollow probe, or pair of hollow probes, used for pick-up of fluid from vials carried by the magazine for transport to the fluid injector sub-assembly. In one aspect, a single hollow probe with upper and lower openings providing a single conduit can be employed which pressurize the fluid contents of a vial after penetration by the probe of a vial transported thereto by the magazine, the probe acting in a second cycle of a timed sequence as a conduit for conveying the fluid contents of the vial to the barrel of the fluid injector sub-assembly. Preferably, a pair of hollow probes are employed, and these can be parallelly or concentrically mounted, but preferably are concentrically mounted. One probe of the pair, in this instance, is generally employed as a conduit to carry gas for pressurizing the contents of a vial, while the other serves as a conduit for the transport of a fluid specimen for a vial to the fluid injector sub-assembly. In either instance, means are thus provided which pressurize the fluid contents of a vial after its penetration by one, or the pair of probes into the vial, and the fluid contents therefrom are conveyed via a conduit to the barrel of the fluid injector sub-assembly.

The probe assembly of said injector feed unit is affixed adjacent to the barrel of the fluid injector sub-assembly, suitably in a fixed location upon the base plate, or housing, with the pointed end of the probe assembly facing downwardly, and it is provided with the drive means for reciprocation and downward movement for penetration of the septum of a vial delivered thereto by the magazine. In all its aspects, it comprises a gas supply conduit with gas inlet and gas outlet means, a fluid specimen supply conduit with fluid specimen inlet means, and outlet means connected to the barrel of said fluid injector sub-assembly, and means for puncturing the septum of a fluid specimen containing vial. In its preferred aspects, the gas supply and fluid specimen supply conduits are mounted concentrically one member with respect to the other, the outer member of the pair being shaped in the form of a needle, the apex or pointed end serving as a means for puncturing the septum of a vial for removal and transfer of fluid specimen to the barrel of the fluid injector sub-assembly.

(c) The magazine is comprised of a closed loop, flexible roller chain mounted upon a floor plate, particularly one which can be removed from the instrument for replacement of empty vials with filled vials and then reinserted. The roller chain is guided along the surface of the floor plate in a fixed path via a series of sprockets or guide rolls, or both, and is driven in such path suitably by motor means associated with one of the sprockets which is driven by the motor. The roller chain is comprised of multiple, repeating links joined together in tandem, the roller portions thereof being oriented relative to the sprockets, or rollers so that the outer plates which, with the rollers, form the links carry open-end tubular vial transport members. The vials are carried in seriatim past a station for pick-up of fluid specimen therefrom by the probe assembly of the injector feed unit.

The characteristics of a preferred automatic fluid injector, and its principle of operation, will be more fully understood by reference to the following detailed description, and to the attached drawings to which reference is made in the subsequent description. Similar numbers are used in the different figures to represent similar parts or components, and subscripts are used with numbers where there is a plurality of similar components. Reference by use of a whole number to a component represented by a number characterized in the description as having a plurality of similar components is intended in a generic sense.

FIG. 5 depicts, in partial section, a right side elevation view of a preferred automatic fluid injector which includes a housing which contains as principal components (a) a fluid injector sub-assembly, (b) an injector feed unit, which includes a probe assembly of preferred type, and (c) a chain drive type magazine of the type referred to with reference to preceding FIGS. 1 through 4 which can be slidably inserted and locked within the housing. (FIG. 2A is a fragmentary sectional view taken along line 2A—2A of FIG. 5, this figure illustrating the track within which a slidable base, on which the components of the magazine are mounted, can be fitted.)

FIG. 6 depicts in plan the automatic fluid injector, preceding FIG. 5 being a right side elevation view taken along line 5—5 of this figure.

FIG. 7 depicts a left side elevation view taken along line 7—7 of FIG. 6.

Figure 8:
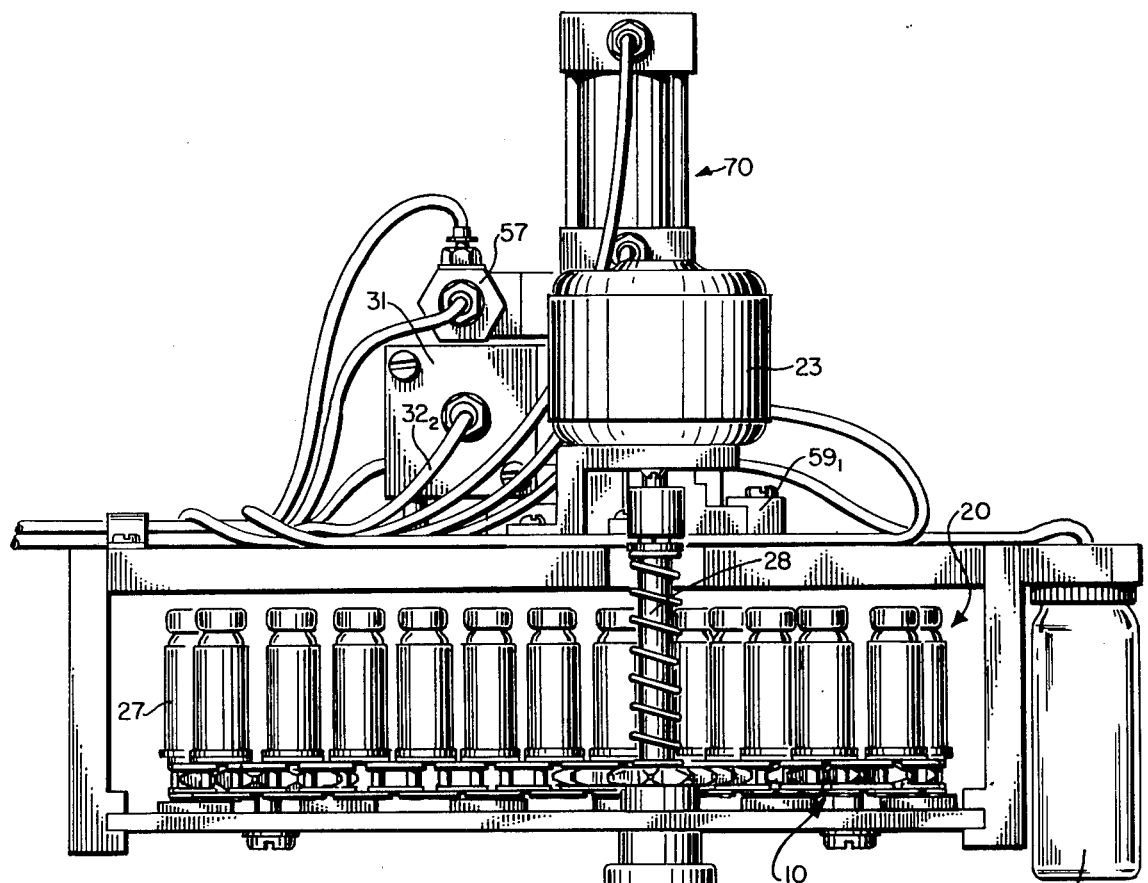

FIG. 8 depicts a rearward sectional view taken along lines 8—8 of FIG. 5.

Figure 9:
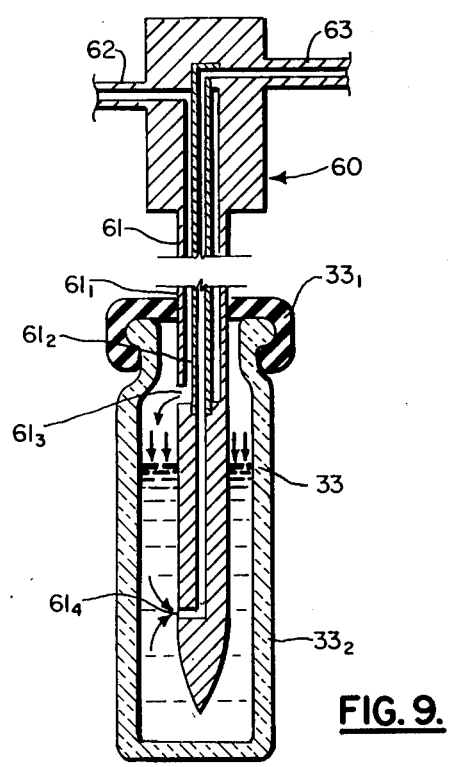

FIG. 9 depicts in some detail a probe assembly of preferred type for use in the pickup, conveyance and delivery of a fluid specimen from a vial carried by the magazine.

Figure 10:
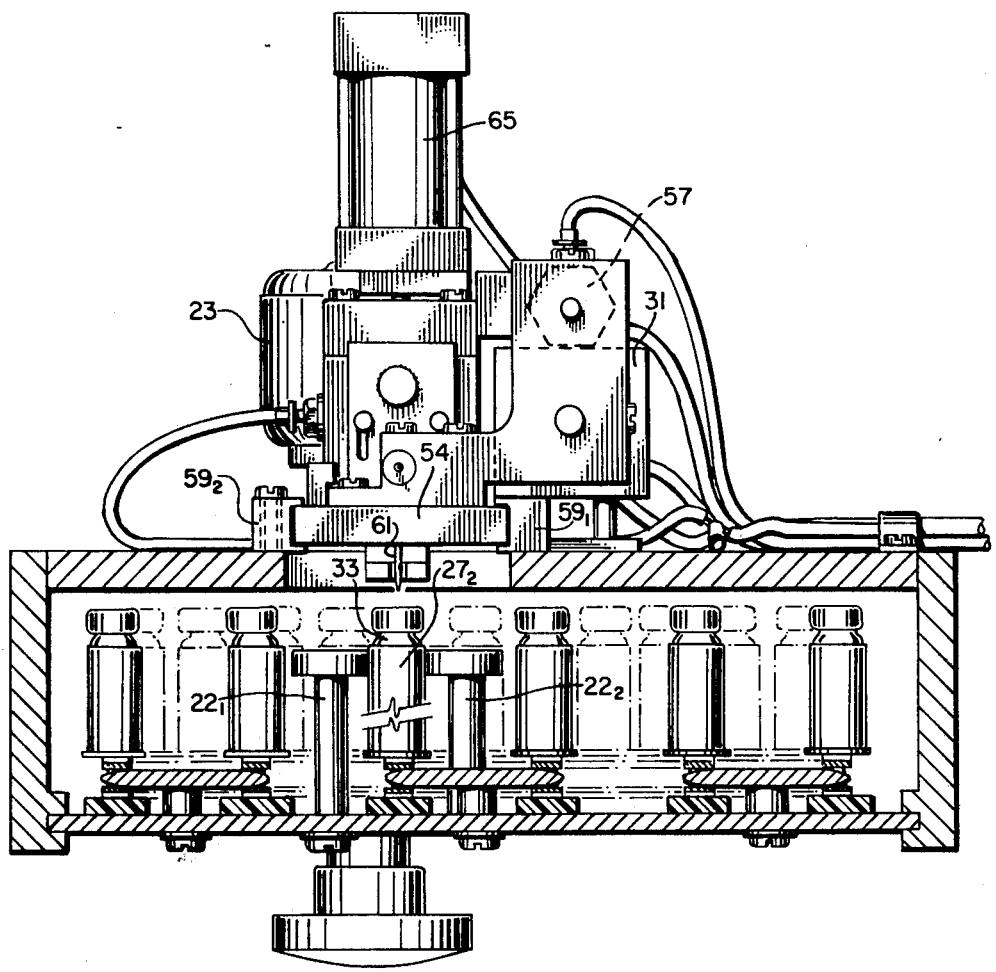

FIG. 10 depicts a cross-sectional view of the automatic fluid injector taken along line 10—10 of FIG. 5.

FIGS. 11 through 15 depict a series of views which, taken together, define the overall function of the automatic fluid injector depicted in FIGS. 1 through 10; particularly in that these views detail the pickup and delivery of a fluid specimen from a vial carried by the magazine.

Figure 1:
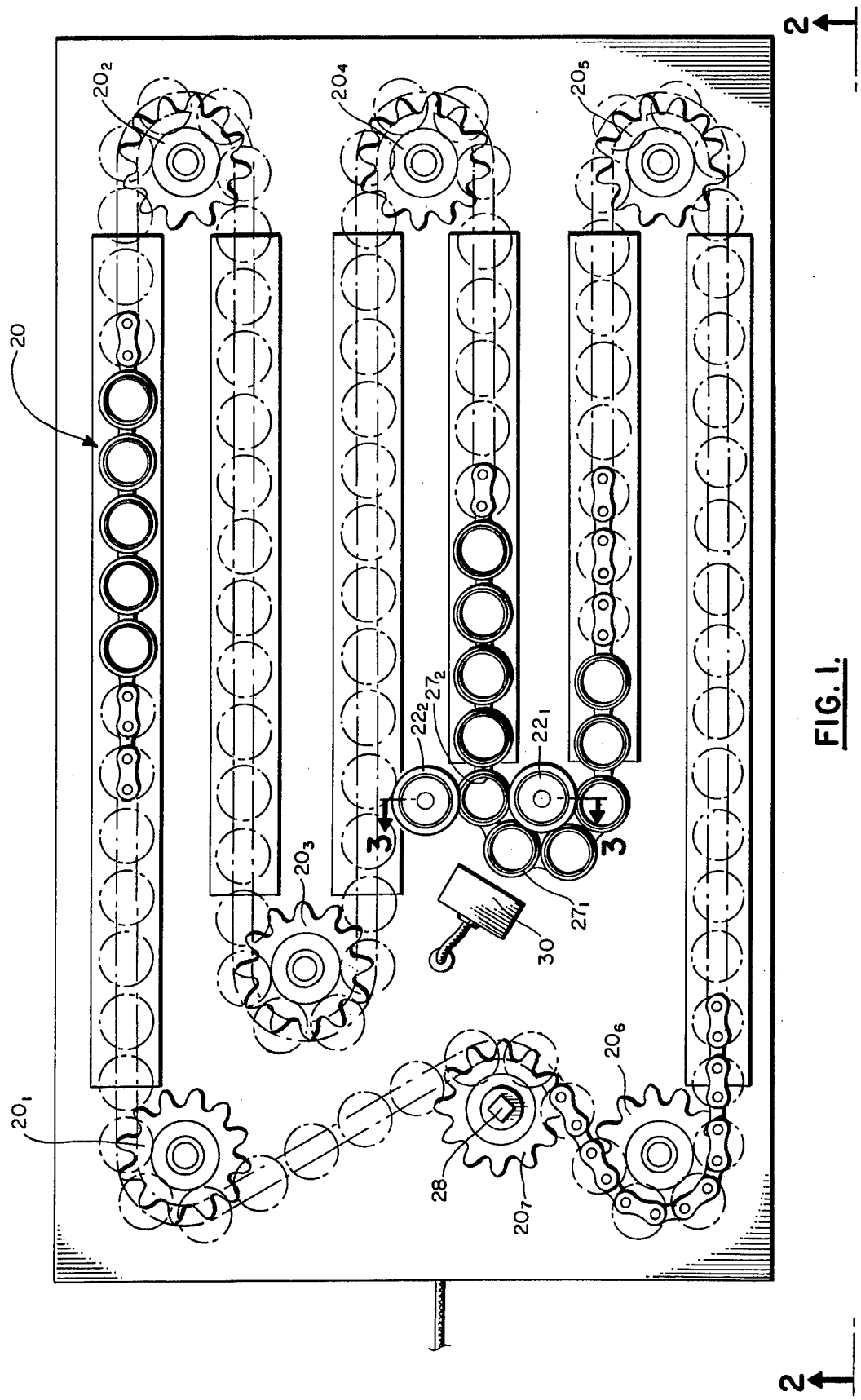
FIG. 1 depicts, in plan view, a preferred type of chain drive type magazine in accordance with the present invention.
Figure 2:
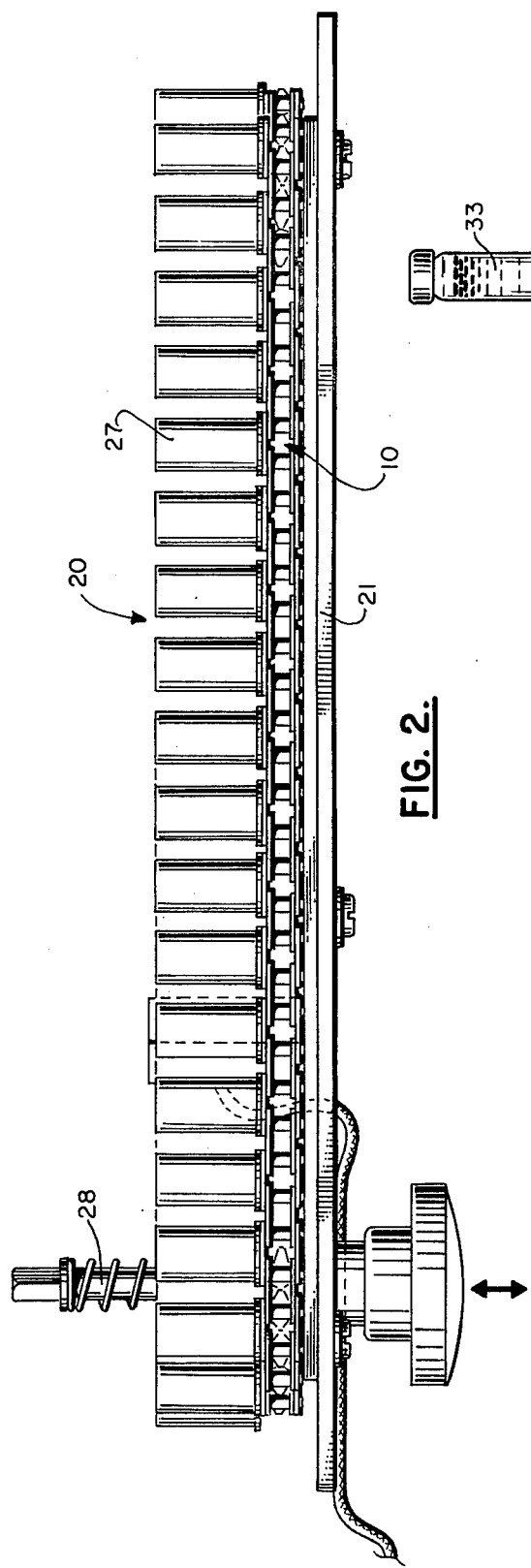
FIG. 2 depicts a right side elevation view of the magazine, this view being taken along line 2—2 of the preceding figure.

Referring first to FIGS. 1 and 2, generally, there is described a preferred chain drive type magazine 20 comprised generally of a driven chain 10 upon which individual fluid specimen filled vials 33 are carried to the injector feed unit 70, and to a station below a fixed probe assembly 60 (constituting a part of the injector feed unit 70) for pickup of fluid specimen for transfer to the fluid injector sub-assembly 50. A closed loop roller chain 10 lies at the heart of the chain drive magazine, the closed loop roller chain 10 being mounted upon a base plate, or floor plate 21. The roller chain 10 is guided upon a series of sprockets $20_1, 20_2, 20_3, 20_4, 20_5, 20_6$, guide rollers $22_1, 22_2$ and a sprocket drive $20_7$ which is driven by suitable motor means, e.g., motor 23. The roller chain 10 is comprised of a system of repeating links joined together in tandem relationship, one link being secured to another to form a continuous, closed chain. Suitably, the roller chain 10 is comprised of mono- or multiple chain linkage, but generally a mono-chain linkage is adequate and preferred.

Figure 4:
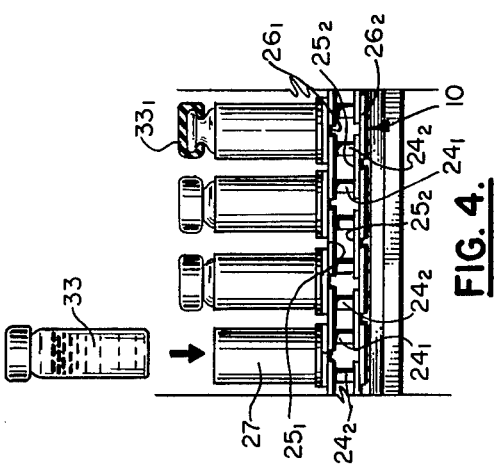
FIG. 4 shows in some detail a segment or fragmentary view of the chain drive type magazine of FIG. 1, with fluid specimen containing vials loaded and carried therein as employed in the operation of the magazine.
Figure 3:
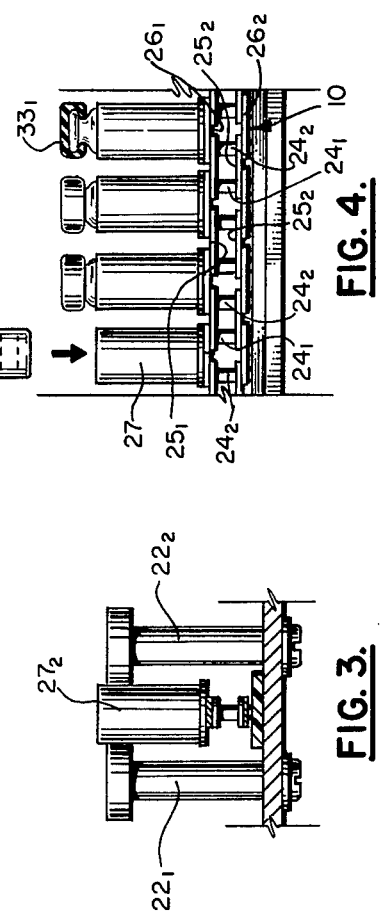
FIG. 3 depicts in cross section a sectional elevation view taken along line 3—3 of FIG. 1.

Referring for convenience to FIGS. 2 or 4, but particularly to the latter figure which provides a fragmentary view depicting in some detail the chain and the manner in which the individual vials 33 are transported, there is shown a segment of the roller chain 10 which is characterized as constructed of a series of links formed of parallel aligned paired rollers $24_1, 24_2$ held together in a side-by-side relationship by a pair of outer plates $25_1, 25_2$ of equal and uniform length, with end openings through which pins are passed to retain the rollers 24 and plates 25 in place; and each of the links are held together in tandem relationship one to another via the outer plates $26_1, 26_2$. The pins are usually set within larger diameter bushings, of somewhat shorter length, and these can be held in place by cotter keys located within lateral openings drilled through the end portions of said pins, or by bifurcated metal clips or retaining rings which fit within circumferential slots located within and about the terminal end portions of said pins, and the like. An upwardly opened end tubular member 27 is affixed to the upwardly faced side of each of the outer plates $26_1$, these members 27 providing chambers or containers within which the individual vials 33 are transported.

Continuing to refer to FIG. 2, the chain drive magazine, inclusive of roller chain 10, vial transport chambers 27, guide rollers $22_1, 22_2$ and sprockets 20 are permanently mounted upon the floor plate 21, the roller chain 10 generally being supported upon a segment of low friction material located on the upper face of the floor plate 21. The magazine 20 can be readily removed from the housing to remove empty vials 33 and to charge freshly filled vials 33, whereupon the floor plate 21 can then be reinserted in place within the housing. The drive sprocket $20_7$ is retained in place upon the floor plate 21 via a lock shaft 28 which not only serves as a release for removal of the magazine 20 from the instrument housing, and for retaining the magazine 20 securely in place after insertion into the instrument housing, but also as a means for coupling the sprocket $20_7$ to the motor 23.

FIG. 1 also depicts means for indexing the vial transport chambers 27 in seriatim, one-by-one in precise location beneath the probe assembly 60, of the injector feed unit 70, for pickup of fluid from a vial 33. This is accomplished by means of a reader 30 which projects a beam of light which it picks up when the beam is reflected back by an indicia mark, properly located on each of the vial transport carriers 27, the pickup by the reader 30 of the reflected light operating mechanism (not shown) which de-energizes the motor 23 to stop the movement of the roller chain 10 at the precise moment, and on station. As specifically shown in this figure, the roller chain 10 is stopped near reader 30 as vial transport carrier $27_1$ is positioned as shown in front of the reader 30. At this point in time the vial carried within the vial transport carrier $27_2$, which is located between rollers $22_1, 22_2$ (FIG. 3), is in position for pickup of fluid specimen therefrom by the probe assembly 60 of the injector feed unit 70.

Referring particularly to FIGS. 5 through 10 there is shown a preferred automatic fluid injector 100 which includes a housing 110 which contains as principal components (a) a fluid injector sub-assembly 50, (b) an injector feed unit 70, inclusive of a preferred type of probe assembly 60, and (c) a chain drive type magazine 20 as described and illustrated by reference to FIGS. 1 through 4, supra. The principal components of the (a) fluid injector sub-assembly 50 include generally a fluid injector per se comprised of a barrel 51, a cannula or hollow needle 52 mounted in the forward end thereof, and a valve 53. The principle components of the (b) injector feed sub-assembly 70 include a reciprocable hollow probe assembly 60, inclusive of a hollow probe per se 61, the function of which is to pick up a fluid specimen from a vial 33 delivered in position thereunder by (c) the magazine, for transport to the barrel 51 of the fluid injector sub-assembly 50. Portions of the fluid specimens from the vials are injected into a media, suitably the septum inlet 120 of an analytical instrument, e.g., gas chromatograph, mass spectrograph or the like. The sub-assemblies (a), (b) and (c) are contained in whole or in part, generally, within a casing, or housing 110 and responsive to controls such as described in U.S. Pat. No. 3,754,443.

The principal features and overall function of these several sub-assemblies and their relation one to another are as follows:

(a) The fluid injector sub-assembly 50 is employed for accurately measuring out a preselected quantity of a fluid specimen for delivery to the septum inlet 120 of an analytical instrument. This sub-assembly includes generally a fluid injector per se which is comprised of a tubular component or barrel 51, a cannula or hollow needle 52 which is slidably mounted within the front end of said barrel 51, and a valve 53 the function of which is to convey fluid to said barrel, and thereafter to trap an increment of the fluid specimen for injection into said septum inlet. In its preferred aspects these several components, barrel 51, needle 52 and valve 53, are mounted upon a plate 54 which is slidably mounted upon a base plate 55 which constitutes a portion of the instrument housing 110.

The barrel 51 and needle 52 are necessarily movable one member relative to the other and hence suitably the needle 52 is mounted in a fixed relationship to the slide plate 54 such that any relative movement between the barrel 51 and needle 52 causes the rearward end of the needle 52 to slide into the barrel 51 and consequently occupy a portion of the volume inside the barrel. Suitably, the needle 52 is secured to the slide plate 54 via the clamp 56 (set screw $56_1$ retaining the needle therein), one end of which is affixed upon the slide plate 54 and the other end of which is affixed upon the forward end of the piston rod $31_2$ of piston unit 31.

Suitably, as best illustrated by reference to FIGS. 12, 13, the rearward end of the needle 52 is provided with a circumferential seal $52_1$ affixed thereon to prevent leakage of fluid around the annulus of the needle as barrel 51 is moved thereupon.

The valve 53 is affixed at the rearward end of barrel 51, its function being to open and close the barrel 51 to the flow of a fluid specimen delivered thereto. In operation, when valve 53 is open a fluid specimen can be flowed through the barrel 51 and needle 52, and closure of the valve 53 will interrupt this flow. On closure, a portion of the fluid specimen can be trapped within the barrel 51 and needle 52, this being the manner that the fluid injector is readied for subsequent injection of fluid specimen through the dispensing end $52_2$ of needle 52.

Virtually any valve which can be controlled in response to a signal, particularly an electrical signal, to provide an on and off position, can be employed. Suitably, the valve employed is an electrically controlled fluid actuated valve 53, e.g., a single acting fluid actuatable piston unit. Referring for convenience to FIGS. 12 and 13, the valve 53 is comprised of a body, or block $53_1$, which is provided with a pair of tubular openings $53_2,53_3$ communicated one with the other via a central channel $53_4$. The tubular opening $53_3$ is provided with a tubular packing $53_5$, the axial opening $53_6$ of which is communicated with a tubular segment $53_7$ inserted therein, the latter being held in place via a lock screw $53_8$. A lateral opening which enters into the axial opening $53_6$ of packing $53_5$ is connected with a tubular segment $53_9$ which enters into the rear of barrel 51. The tubular opening $53_2$ is closed at the top by a plate $53_{10}$ by screws $53_{10A},53_{10B},53_{10C},53_{10D}$ which secures said top to the valve body $53_1$, and holds said valve in place on the slide plate 54. A piston $53_{11}$, inclusive of a head $53_{11A}$, and stem $53_{11B}$, provides the closure element for the valve. The head $53_{11A}$, with its circumferential O-rings $53_{12A},53_{12B}$, is snugly fitted within the tubular opening, the stem $53_{11B}$ extending into the communicating channel or opening $53_4$ entering partially into the axial opening $53_6$ of tubular packing $53_5$. The head $53_{11A}$ of the piston, in FIG. 13, is biased in closed position by a spiral spring $53_{13}$ which is seated between the inner face of valve top plate $53_{10}$ and the outer face of head $53_{11A}$ of the piston $53_{11B}$. The function of this valve will be quite clear by continued reference to FIGS. 12 and 13. With reference to FIG. 12, on entry of a pressurized gas, e.g., air or nitrogen, into the valve body via opening $53_{14}$, located within channel $53_4$, the pressure exerted by the helical spring $53_{13}$ is overcome and the valve is opened by withdrawal of the stem $53_{11B}$ from the junction between openings $53_6,53_{15}$ and a fluid specimen can ingress through these openings to fill the barrel 51 and needle 52. Conversely, when no pressurized gas is admitted through the opening $53_4$, the helical spring $53_{13}$ causes extension of stem $53_{11B}$ into the junction formed by openings $53_6,53_{15}$, thus closing off the flow of fluid specimen into the barrel 51 and needle 52 (FIG. 13).

The fluid injector sub-assembly 50 also includes means for actuating and reciprocating the barrel 51 relative to needle 52, suitably drive means which can be actuated and controlled in response to a signal, especially an electrical signal. Such means is, suitably, a piston, particularly a fluid actuatable double piston unit 57 mounted alongside valve 53 and barrel 51, both of which are carried upon slide plate 54. The piston unit 57, as shown, e.g., in FIG. 6, is comprised of an outer cylinder $57_1$ with its included piston, inclusive of rod $57_2$ and fixed head (not shown). The piston unit 57 is secured to the slide plate 54 via attachment through piston rod $57_2$ to an L-shaped bracket 58 which is secured to the side of valve 53 such that the piston unit 57 forms an integral part of the fluid injector sub-assembly 50. Movement of barrel 51, relative to and without corresponding movement of the needle 52, can be produced by reciprocation of, inter alia, the valve 53 and barrel 51 without corresponding movement of slide plate 54. Such reciprocal movement is produced by alternate injections of a pressurized fluid, e.g., a gas such as air or nitrogen, via lines $58_1$ and $58_2$. The valve 53 and barrel 51 are moved forward (and fluid specimen injected) when pressurized gas is injected into the piston unit 57 via line $58_1$, and valve 53 and barrel 51 are moved rearwardly when pressurized gas is injected into the opposite side of piston unit 57 via line $58_2$.

Drive means for actuating and reciprocating the entire fluid injector sub-assembly 50, inclusive of slide plate 54 and its affixed components, is also required. In its preferred aspects, the slide plate 54 is slidably mounted upon the base plate 55 via means of guide ways $59_1, 59_2$ which are fitted along the longitudinal edges of a rather wide opening cut through the base plate 55, the slide plate 54 riding, being retained, and properly positioned within the guide ways $59_1,59_2$. The slide plate 54, with valve 53, barrel 51 and needle 52, as a unit is reciprocably movable within said slot by means of piston unit 31, as suggested. A fluid actuatable piston unit 31 is thus mounted on the lower side of piston unit 57, and upon base plate 55, and it is operatively associated with slide plate 54, its function being to reciprocate the entire slide plate 54 along a guided path for insertion, and withdrawal, of the dispensing end $52_2$ of needle 52 into a suitable media, e.g., a spetum inlet 120 of an analytical instrument, into which a preselected, accurately measured quantity of a fluid specimen is to be injected. Referring, e.g, to FIG. 7, it will thus be observed that the piston unit 31 is comprised of an outer cylinder $31_1$ with its included piston, inclusive of rod $31_2$ and head (not shown). The rod $31_2$ of piston unit 31 is attached via a suitable mounting bracket 56 to the slide plate 54 such that pressurized gas injected via line $32_1$ into the rearward end of said piston unit 31 causes movement of the slide plate 54 forward to thrust needle 52 into inlet 120 and, conversely, gas injected via line $32_2$ into the opposite, or forward, end of the piston unit 31 causes movement of the slide plate 54 in the opposite direction to withdraw needle 52 from spetum inlet 120.

The fluid injector sub-assembly also includes a fluidic diversion valve shown, e.g, by reference to FIG. 12. The purpose of fluidic diversion valve 40 is to collect and transfer fluid specimen ejected from barrel 51 and needle 52 as occurs during the cleaning, purging and filling steps. Referring specifically to FIG. 12, it will be observed that the fluidic diversion valve 40 is constituted as a generally tubular member, preferably formed of a resilient plastic or plastic-like material, suitably a self-sealing semi-rigid or rigid plastic such as polytetrafluoroethylene (Teflon). It is provided with an axial opening $40_1$, at least one and suitably a pair of lateral inlet openings $40_2, 40_3$ and at least one, suitably one lateral outlet opening $40_5$. The openings $40_2, 40_3, 40_4$ are of at least equal, but preferably larger, diameter than axial opening $40_1$ such that when a gas, e.g., air or nitrogen, is introduced into inlets $40_2,40_3$, the gas will sweep out the annulus between the external needle wall and inside wall of the axial opening $40_1$ and convey fluid specimen through the outlet opening $40_4$. Suitably, a seal is formed within the openings $40_2, 40_3$ via use of a bifurcated metal member 41, provided with prongs $41_2, 41_3$ which fit within openings $40_2, 40_3$ (FIG. 14), and a purge gas is conveyed thereto via tubing 42. Liquid is removed from the outer dispensing end $52_2$ of needle 52 and conveyed via tubing 43 to slop bottle 44, the latter being connected to outlet opening $40_4$ via connection to the metal tube 45 which is snugly fitted within opening $40_4$.

Figure 11:
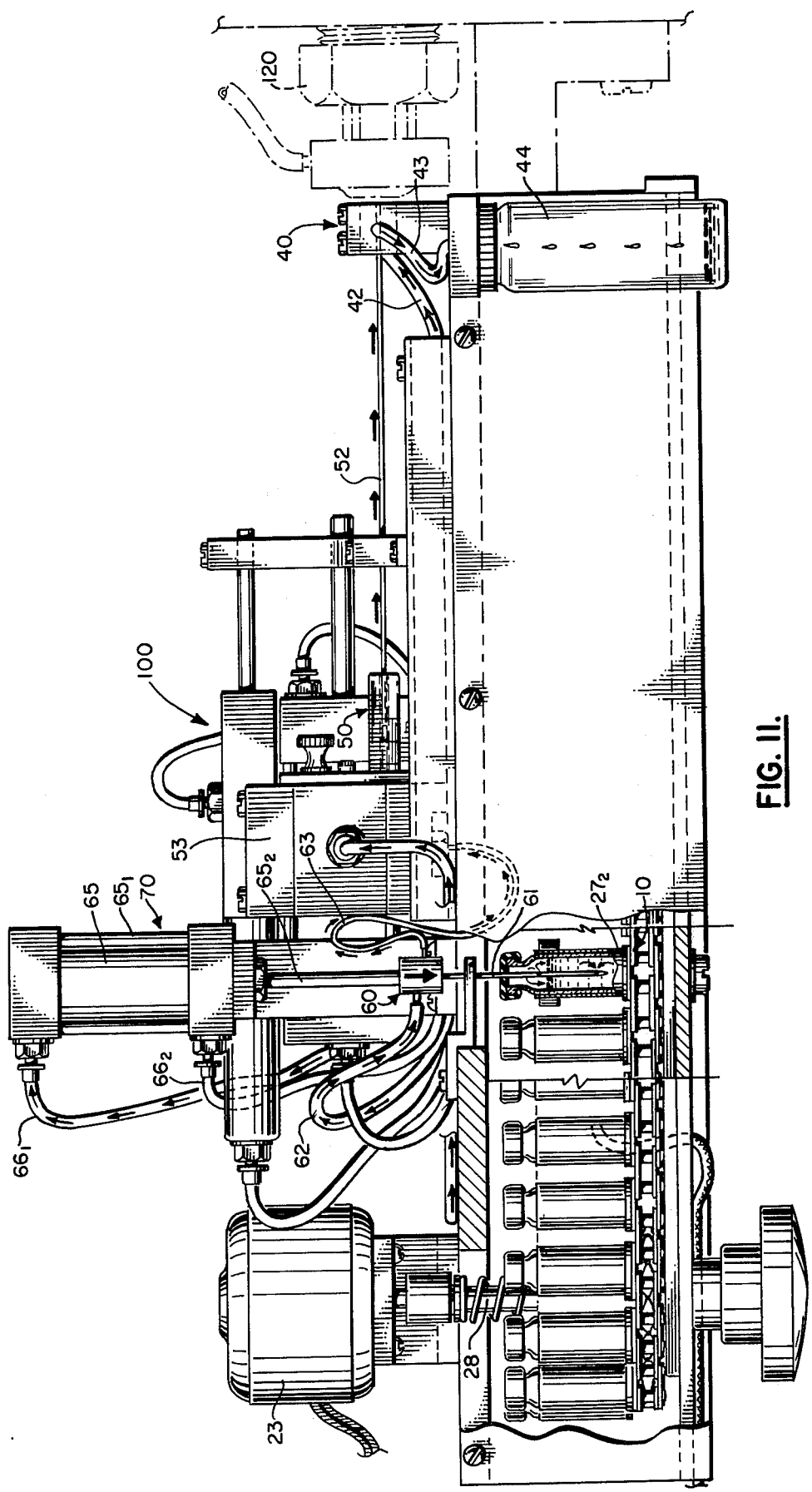

(b) The principle components of the injector feed assembly 70 are best shown by reference to FIGS. 5, 10 and 11. These several components include generally a preferred type of probe assembly 60 which is mounted, or affixed, to the base plate 55, rearwardly of slide plate 54, with the pointed end of the probe assembly 60 per se facing downwardly into the magazine compartment, or magazine 20, wherein filled vials 33 are transported by the magazine and arranged for pick-up, in seriatim, by the probe of a portion of the fluid specimen therefrom, for delivery to the fluid injector sub-assembly 50. The septum $33_1$ of a vial 33 can be pierced by the pointed end of the probe on descent thereof at a station wherein the vials 33 are positioned in seriatim, descent of the probe assembly 60 being occasioned by actuation of piston unit 65.

The piston unit 65, like piston unit 31, as shown, e.g., by reference to FIG. 11, is comprised of a cylinder $65_1$ with its piston, inclusive of piston rod $65_2$ and head (not shown). The piston unit 65 is vertically mounted in fixed position, the probe assembly 60 being mounted on the forward end of the piston rod $65_2$ for actuation and movement thereof in timed sequence for pick-up and delivery of fluid specimen from vials 33 delivered by magazine 20. Pressurized gas, e.g., air or nitrogen, injected into line $66_1$ causes movement of the probe assembly 60 downwardly (gas being expelled via line $66_2$) and, conversely, gas injected into line $66_2$ causes ascent of the probe assembly 60 (gas being expelled via line $66_1$).

Referring now, for convenience, to FIG. 9, there is described a preferred type of probe assembly 60 used for withdrawing a fluid specimen from a vail 33 delivered on station by roller chain 10 of magazine 20. The hollow probe portion, or probe 61, per se of probe assembly 60 is shown projected into a vial 33 which contains a fluid specimen held in place by an elastic or rubber septum $33_1$ located on top of a glass bottle $33_2$; which fluid is to be delivered to the fluid injector sub-assembly 50. The hollow probe 61 is, in effect, constituted of a pair of hollow needles $61_1$, $61_2$ concentrically mounted, an inner needle $61_2$ contained within a larger diameter outer needle $61_1$. An annular opening, or passageway, between the inner and outer needles $61_1$, $61_2$, provides an internal conduit within which a pressurized gas, e.g., air or nitrogen, can be transmitted via a connecting tube 62, the gas entering the vial 33 via the uppermost opening or exit port $61_3$. The gas cannot escape, and hence the fluid contents of the vial are pressurized by the entering gas, the gases exerting a downward pressure. This pressure forces the fluid specimen into the lower entry port $61_4$, the fluid specimen ascending through the axial opening through inner needle $61_2$, the fluid exiting via an outlet to the connecting tubing 63.

(c) The function of the magazine 20, which is located in a chamber within the lower portion of the instrument housing 110, is to convey fluid specimen containing vials 33 in timed sequence, and in seriatim, to a station below the probe assembly 60, of the injector feed unit 70, for pick-up and transfer of fluid specimen to the barrel 51 of the fluid injector sub-assembly 50. As suggested in the previous and specific reference to FIG. 1, when the magazine 20 is locked in position within the instrument housing, a vial 33 carried by vial transport carrier $27_2$ (and located between rollers $22_1$, $22_2$) is stopped via the action of reader 30, positioned and stationed directly below the probe assembly 60 of injector feed unit 70. In this position, as shown by reference, e.g., to FIG. 10, the pointed end of the hollow probe 61 is poised just above the upper septum end of a vial 33 contained within vial transport carrier $27_2$ (between rollers $22_1$, $22_2$). Downward movement, or descent of the hollow probe 61 will cause penetration of the septum of the vial 33 by the pointed or tapered end of the probe 61, and entry thereof into the vial as illustrated by reference to FIG. 9. As the vials 33 are introduced in seriatim into position beneath the probe assembly 60, the probe 61 is thrust downwardly by actuation of piston unit 65, the pointed end thereof penetrating, or passing through, the septum for pick-up and delivery of the fluid specimen to the barrel 51 of the fluid injector sub-assembly 50.

An operating cycle is described by reference to the figures, particularly to FIGS. 11 through 15, these figures depicting a series of views describing the cleaning and purging, filling and injection of an accurately measured fluid specimen obtained from a vial delivered by the magazine. The cycle can be repeated in time sequence ad infinitum, as follows:

(a) Referring initally to FIG. 11, a cleaning and purging portion of an operating cycle is described. The injector feed sub-assembly 70 is activated by injection of pressurized gas via line $66_1$ into piston unit 65 causing downward thrust of piston rod $65_2$ and probe assembly 60. The septum $33_1$ (FIG. 9) of the gas tight vial 33 is penetrated by the sharp, pointed end of hollow probe 61 which moves downwardly into the vial 33 until port $61_4$ is submerged in the liquid, and port $61_3$ is at least within the vapor space between the surface of the liquid and the septum $33_1$. Pressurized gas injected via line 62 into the annulus between needles $61_1$, $61_2$ enters into the vial 33 via port $61_3$ effectively pressurizing the vial, this causing fluid specimen contents to enter into port $61_4$, ascend through the bore of the needle 61, and exit via tubing 63. The fluid specimen is conveyed via the tubing 63 to the valve 53 which, at this point in time, is in open position (FIG. 12); the valve having been opened and retained in open position by pressurized gas injected through the port $53_{14}$.

Referring for convenience to FIG. 12, the fluid specimen is passed through line 63, inlet $53_7$ and openings $53_6$, $53_{15}$ into the rear of barrel 51. The fluid passes into the rearward end of said barrel 51 and then through the bore of needle 52, the flowing stream of fluid cleaning and purging the barrel 51 and needle 52 of any contamination, as may be present from a previous injection with a different fluid specimen.

The needle 52 of the fluid injector sub-assembly 50 is shown in a position of withdrawal from the septum inlet 120, the dispensing end $52_1$ thereof being located within the fluidic diversion valve 40. A gas, e.g., air or nitrogen, is passed via line 42 through the openings within the bifurcated tubular member 41, the gas cleaning and carrying away excess fluid via the tubular member 45, and line 43, the fluid emptying into the slop bottle 44.

(b) To close the valve 53, and complete the cleaning and purging step of the sequence, the flow of pressurized gas to the valve 53 via opening $53_{14}$ is stopped, this releasing the tension on helical spring $53_{12A}$. As this occurs, the helical spring $53_{12A}$ (formerly under tension as depicted in FIG. 12) urges the piston head $53_{11A}$ inwardly (FIG. 13), the piston rod $53_{11B}$ being thrust past the junction of axial opening $53_6$ and lateral opening $53_{15}$, this cutting off the flow of fluid specimen via line 63 into inlet $53_7$, and openings $53_6$, $53_{15}$ at the rearward end of barrel 51. In interrupting the flow in this manner, after the barrel 51 and needle 52 have been purged and cleaned, an uncontaminated portion of the fluid specimen is trapped within the barrel 51 and needle 52 of the fluid injector sub-assembly 50.

(c) The purging, cleaning and filling functions of fluid injector sub-assembly 50 having been completed, the probe 61 can at this time be withdrawn from vial 33 of vial transport carrier $27_2$ and repositioned for use in the subsequent cycle. Withdrawal of the probe 61 is accomplished by injection of pressurized gas via line $66_2$ into piston unit 65 (gas being expelled via line $66_1$). A new vial is then introduced into position by the magazine 20 for pick-up by the probe assembly 61 in the next cycle of operation.

Figure 14:
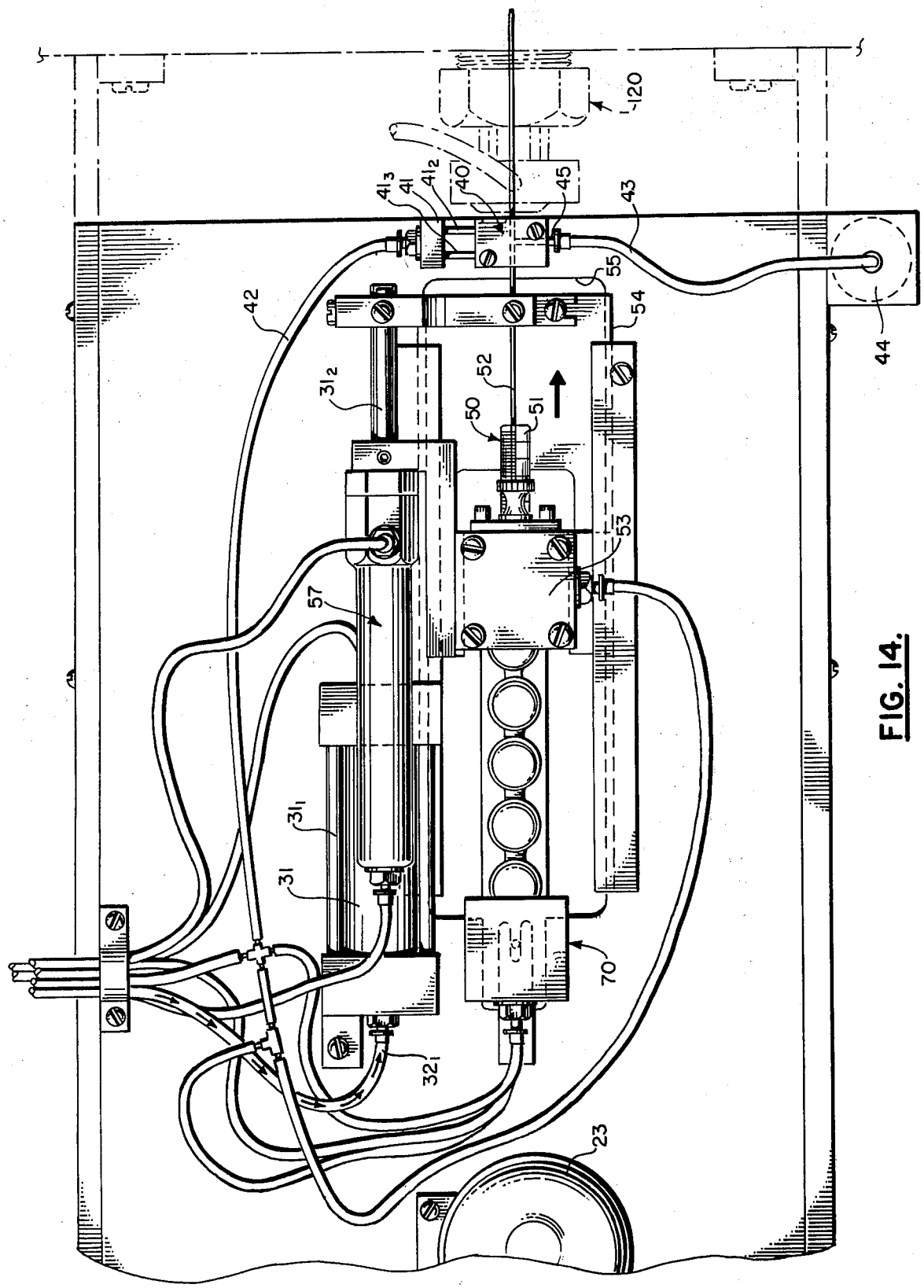
Figure 15:
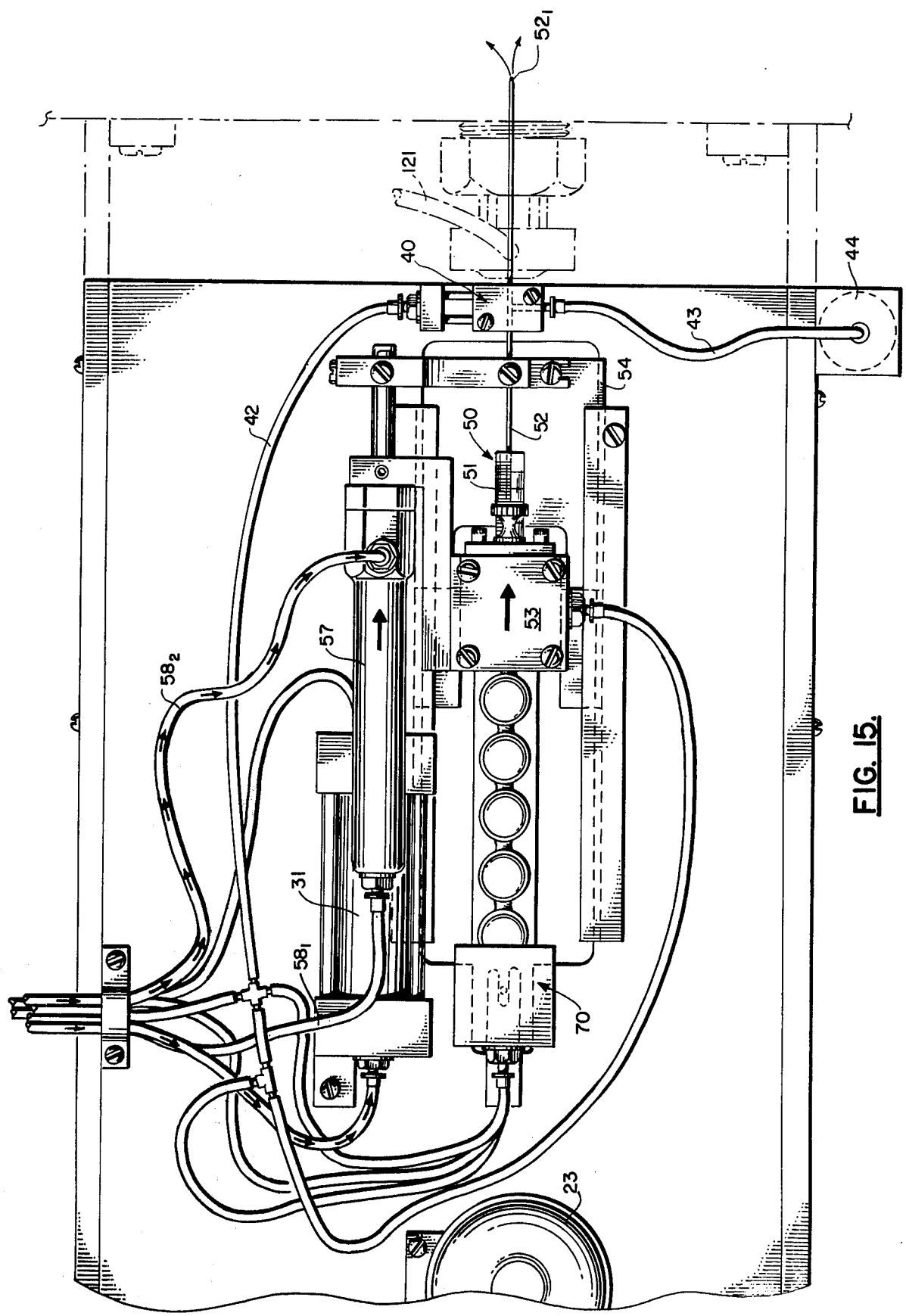

(d) To initate the sequence required for the actual injection of the fluid specimen, the fluid injector sub-assembly 50 as a unit, inclusive of barrel 51, needle 52, valve 53, and piston 57, carried on slide plate 54, is moved forwardly by transport or movement of slide plate 54. Referring initially to FIG. 14, pressurized gas is injected via line $32_1$ into piston unit 31, this causing piston rod $31_2$ to be thrust outwardly and forwardly (as gas is expelled from the opposite side of the piston unit 31 via line $32_2$). Outward thrust of piston rod $31_2$ carries the slide plate 54 forwardly and thrusts the needle 52 deeply into septum inlet 120 of an anlytical instrument, e.g., a gas chromatograph. (e) The actual injection step is shown by reference to FIG. 15. Injection is accomplished by means of the piston unit 57. Pressurized gas is injected via line $58_2$ into the forward end of the unit, this causing forward thrust and movement of the valve 53 and barrel 51 without corresponding movement of the needle 52 which is held in fixed position. The barrel 51 is thus moved relative to the needle 52 and the rearward end of the latter is thrust inwardly into the barrel 51 to displace fluid speciment from the dispensing end $52_1$ of the needle 52. The fluid specimen, in measured amount, is thus injected into the septum inlet 120 and conveyed into the instrument via carrier gas introduced at line 121. It is quite evident that the volume of fluid specimen actually injected is equal to the volume of the fluid specimen displaced by the rearward end of the needle 52 on its movement into the barrel 51.

(f) After injection of the fluid specimen, the barrel 51 of the fluid injector sub-assembly 50 is repositioned in relation to needle 52, as prior to initiation of step (e) wherein the barrel 51 was slid over the rear end of the needle 52 to eject the fluid specimen. This is accomplished by injecting pressurized gas via line $58_1$ to cause rearward movement of piston unit 57 which moves the barrel 51 and valve 53 rearwardly while the needle 52 is held in fixed relative position.

(g) The slide plate 54 is then repositioned rearwardly, and needle 52 withdrawn from the septum inlet 120 by injection of pressurized gas via line $32_2$ into the front end of piston unit 31 (while gas is expelled via line $32_1$). [At this point in time this probe assembly 60 could be repositioned, and a fresh via delivered by magazine 20 for pick-up in lieu of such step having been previously conducted as in Step (c).]

It is apparent that various modifications and changes can be made without departing the spirit and scope of the present invention. The apparatus is constructed of materials substantially inert or nonreactive to the chemical or corrosive action of the fluid specimens to be measured and dispensed. The barrel of the fluid injector is normally constructed of glass, but can be constructed of a plastic or plastic-like material. The seals and tubing used in the instrument are normally constructed of rubber or plastic, and the rest of the instrument of various metals.

The seals are preferably formed of a rigid or semi-rigid, resilient form of plastic or plastic-like material. The self-lubricated plastics are especially preferred in this capacity, and can also be applied as a laminate or protective film. The polyfluorinated ethylene polymers, notable among which is polytetrafluoroethylene (Teflon), are particularly outstanding. Conventional resilient or elastic-like materials, such as natural or synthetic rubbers, can also be employed.

The fluid injector sub-assembly (except for the barrel), the injector feed assembly, particularly the needle and probes, the piston units, and the like, are preferably constructed of metals, e.g., ferrous metals such as iron, iron alloys, steel, stainless steels, and the like; or such metals as aluminum, magnesium, brass, copper, bronze, chrome, alloys of these and other metals, and the like.

It is apparent that various changes, such as in the absolute or relative dimensions of the parts, materials used, and the like, as well as the suggested mode or particular sequence of withdrawing or delivering fluids, can be made without departing the spirit and scope of the invention, as will be apparent to those skilled in this art.

Having described the invention, What is claimed is:

1. In a fluid injector, or apparatus, for withdrawing fluid specimens from fluid specimen containing septum type vials for repetitively measuring and injecting preselected quantities of fluid specimens into a medium such as an inlet to an analytical instrument, the combination comprising
a base plate, constituting a portion of a housing, which can be mounted adjacent the inlet to the analytical instrument,
  (a) a fluid injector sub-assembly, inclusive of
    a syringe barrel,
    a hollow needle mounted on an end of the barrel providing an opening from the dispensing end of said needle through said needle and barrel, and
    means for introducing fluid specimen into said barrel and needle, and means for ejection of an accurately measured quantity of said fluid specimen from said barrel through said needle into the inlet of said analytical instrument,
  (b) an injector feed sub-assembly, inclusive of
    a probe assembly affixed upon said base plate comprising
      a gas supply conduit with gas inlet and gas outlet means,
      a fluid specimen supply conduit with fluid specimen inlet means, and outlet means operatively associated with the barrel of said fluid injector sub-assembly for introducing fluid specimen thereto, including means for actuation and reciprocation of said probe assembly, and means for puncturing the septum of the fluid specimen containing vial so that the gas and fluid specimen supply conduits can enter into and lie within the vial, and
  (c) a magazine sub-assembly, inclusive of
    a floor plate mounted within said housing below said base plate and probe assembly,
    a plurality of sprockets, with gear teeth, rotatably mounted upon said floor plate, the plane of rotation of said sprockets being parallel to the plane of orientation of said floor plate,
    a flexible closed loop roller chain comprised of a series of links aligned in tandem, each link of the chain including a pair of parallel aligned, spaced apart rollers equal in length and vertically oriented with respect to said floor plate, secured together by a plate mounted on each side of said pair of rollers, the openings in the chain between the rollers being meshed with and guided upon said sprockets, a plurality of open end vial transport containers, vertically oriented with the open ends facing upwardly, mounted upon upwardly facing plates which form the links of the roller chain, a motor mounted on said base plate, the output shaft of which is geared to at least one of said sprockets for driving said roller chain through its closed fixed path, a means for stopping each of said vial transport containers in sequence at a pick-up station below, and in the path of said probe assembly for penetration of the septum of a vial by said probe assembly, whereby a pressurized fluid can be injected through the probe into the vial to pressurize the fluid specimen contained therein, the fluid specimen then transferred from the vial via the hollow probe to the barrel of said fluid injector with a preselected quantity of the fluid specimen for subsequent injection into the inlet of the analytical instrument.

2. The apparatus of claim 1 wherein the combination includes a slide plate reciprocably, unidirectionally movable upon said base plate, means for reciprocation of said slide plate, (a) the fluid injector sub-assembly includes a hollow needle affixed to said slide plate, the needle being slidably mounted within an end of the barrel so that said barrel is movable relative to said needle, a valve located at the opposite end of said barrel for opening said barrel to permit ingress of a fluid specimen into said barrel and needle, and for closing said barrel and needle, and means for moving said barrel relative to the needle on closure of said valve.

3. The apparatus of claim 1 wherein (a) the fluid injector sub-assembly includes a hollow needle affixed to said slide plate, the needle being slidably mounted within an end of the barrel so that said barrel is movable relative to said needle, a valve located at the opposite end of said barrel for opening said barrel to permit ingress of a fluid specimen into said barrel and needle, and for closing said barrel and needle, and means for moving said barrel relative to the needle on closure of said valve, and (b) the injector feed sub-assembly includes a probe assembly characterized as one which is comprised of a pair of concentric hollow conduits, one of which serves as a gas supply conduit inclusive of a gas inlet and gas outlet, and the other of which serves as the fluid specimen supply conduit inclusive of a fluid specimen inlet, and a fluid specimen outlet which is operatively connected through the valve at the rearward end of the barrel of said fluid injector sub-assembly, the outer conduit being shaped in the form of a needle with the pointed end faced downwardly to provide means for puncturing a septum of a septum type fluid specimen containing vial transported thereto by the magazine for extension of said probe assembly into the interior of said vial, whereby, on opening the valve of the fluid injector sub-assembly, the fluid specimen contents of the vial can be pressurized by injection of gas into the vial via the gas inlet conduit and fluid specimen transported via the fluid specimen outlet of the probe assembly through the valve to clean and purge the barrel and needle, the valve can then be closed to trap an accurately measured volume of the fluid specimen within the barrel and needle, the slide plate can then be moved forward to insert the dispensing end of the needle into the inlet of said analytical instrument, and the measured quantity of fluid specimen then injected by activation of said means which moves the barrel forward relative to the needle to displace and inject the fluid specimen via the dispensing end of the needle into the inlet of the analytical instrument.

4. The apparatus of claim 1 wherein a fluidic diversion valve is mounted on the base plate, said fluidic diversion valve comprising a tubular member the axial opening of which is aligned upon the septum inlet of said analytical instrument and adapted for receipt and movement therethrough of the needle of said fluid injector sub-assembly, and a lateral passageway intersecting with said axial opening for carrying away waste fluid specimen ejected from the dispensing end of the needle during a purging and cleaning step, and through which a gas can be injected to dry the dispensing end of the needle prior to insertion of the needle into the inlet of an analytical instrument for an injection.

5. The apparatus of claim 1 wherein, within the magazine sub-assembly, the means for stopping each of said vial transport containers in sequence at said pick-up station for the withdrawal by the probe of fluid specimen from the septum type vials carried therein is comprised of a reader which projects a beam of light which can be reflected back by an indicia mark located on a vial transport container, and picked up by the reader to de-energize said motor to stop the movement of said roller chain at the precise moment, and on station for pick-up by the probe of fluid specimen from a vial carried by an individual transport container.

6. The apparatus of claim 1 wherein (a) the fluid injector sub-assembly includes a hollow needle affixed to said slide plate, the needle being slidably mounted within an end of the barrel so that said barrel is movable relative to said needle, a valve located at the opposite end of said barrel for opening said barrel to permit ingress of a fluid specimen into said barrel and needle, and for closing said barrel and needle, and means for moving said barrel relative to the needle on closure of said valve, and said fluid injector sub-assembly, inclusive of said components of said fluid injector sub-assembly, is slidable upon said base plate via means of parallel aligned guide ways which are fitted along the longitudinal edges of a slot cut within said base plate, and reciprocably movable within said slot via means of a piston unit.

7. In a fluid injector, or apparatus, for withdrawing fluid specimens from septum type vials for repetitively measuring and injecting preselected quantities of fluid specimens into a medium such as an inlet to an analytical instrument, the combination comprising a base plate, constituting a portion of a housing, which can be mounted adjacent the inlet to the analytical instrument, a slide plate reciprocably, unidirectionally movable upon said base plate, means for reciprocation of said slide plate, (a) a fluid injector sub-assembly mounted upon said slide plate, inclusive of a syringe barrel, a hollow needle mounted on the end of the barrel providing an opening from the dispensing end of said needle through said barrel and needle, the needle being sealed, and slidably mounted within the end of the barrel so that the barrel is movable relative to said needle for dispensing the fluid specimen by displacement thereof through the dispensing end of the needle, the hollow needle being affixed to said slide plate, a valve located at the opposite end of said barrel for opening the barrel to permit ingress of a fluid specimen into said barrel and needle, and means for moving said valve and barrel upon said slide plate relative to said affixed needle on closure of said valve, (b) an injector feed sub-assembly mounted on said base plate, inclusive of a probe assembly characterized as one which is comprised of a pair of concentric hollow conduits, one of which serves as a gas supply conduit inclusive of a gas inlet and gas outlet, and the other of which serves as the fluid specimen supply conduit inclusive of a fluid specimen inlet, and a fluid specimen outlet wich is operatively connected through the valve at the rearward end of the barrel of said fluid injector sub-assembly, the outer conduit being shaped in the form of a needle with the pointed end faced downwardly to provide means for puncturing the septum of a septum type vial delivered thereto so that the supply conduits of the probe can enter into said vial, and means for actuation and reciprocation of said probe assembly to puncture the septum of the vial for removing a fluid specimen from said septum type vial, (c) a magazine sub-assembly, inclusive of a floor plate mounted within said housing below said base plate and probe assembly, a plurality of sprockets, with gear teeth, rotatably mounted upon said floor plate, the plane of rotation of said sprockets being parallel to the plane of orientation of said floor plate, a flexible closed loop roller chain comprised of a series of links aligned in tandem, each link of the chain including a pair of parallel aligned, spaced apart rollers equal in length and vertically oriented with respect to said floor plate, secured together by a plate mounted on each side of said pair of rollers, the openings in the chain between the rollers being meshed with and guided upon said sprockets, a plurality of open end vial transport containers, vertically oriented with the open ends facing upwardly, mounted upon upwardly facing plates which form the links of the roller chain, within which septum type vials filled with fluid specimens can be placed with their septum ends faced upwardly, a motor mounted on said base plate, the output shaft of which can be geared to at least one of said sprockets for drivings said roller chain through its closed fixed path, a means for stopping each of said vial transport containers in sequence at a pick-up station below, and in the path of said probe assembly for penetration of the septum of a vial by the pointed end of said probe assembly, whereby a pressurized fluid can be injected through the probe into a vial to pressurize the fluid specimen contained therin, the fluid specimen then transferred from the vial via the hollow probe to the barrel of said fluid injector sub-assembly for cleaning, purging and filling said fluid injector with a preselected quantity of the fluid specimen for subsequent injection into the inlet of the analytical instrument by actuation of said means for reciprocation of said slide plate on which said fluid injector sub-assembly is mounted to thrust the dispensing end of the needle into the inlet of said analytical instrument.

* * * * *